(12) United States Patent
Fung et al.

(10) Patent No.: US 8,419,700 B2
(45) Date of Patent: Apr. 16, 2013

(54) TAMPON OVERWRAP

(75) Inventors: Paul Y. Fung, South River, NJ (US); David L. Kimball, Flemington, NJ (US); Stephan M. Linkel, Ewing, NJ (US); Ralf Mueller, Duesseldorf (DE); Lionel Robbe, Köln (DE); Yang Xu, Hamburg (DE)

(73) Assignees: McNeil-PPC, Inc., Skillman, NJ (US); Johnson & Johnson GmbH, Neuss (DE)

( * ) Notice: Subject to any disclaimer, the term of this patent is extended or adjusted under 35 U.S.C. 154(b) by 717 days.

(21) Appl. No.: 12/621,744

(22) Filed: Nov. 19, 2009

(65) Prior Publication Data

US 2010/0130953 A1     May 27, 2010

Related U.S. Application Data

(60) Provisional application No. 61/118,046, filed on Nov. 26, 2008.

(51) Int. Cl.
 *A61F 13/20* (2006.01)
(52) U.S. Cl.
 USPC ..................... 604/385.02; 604/904
(58) Field of Classification Search ............. 604/385.02, 604/385.17, 385.18, 904; 206/440, 438, 206/495; 229/87.01, 87.05
See application file for complete search history.

(56) References Cited

U.S. PATENT DOCUMENTS

| | | | |
|---|---|---|---|
| 3,092,251 A | 6/1963 | Jaggers | |
| 3,135,262 A | 6/1964 | Kobler et al. | |
| 3,278,013 A | 10/1966 | Banks | |
| 3,309,006 A | 3/1967 | Perry et al. | |
| 3,766,703 A | 10/1973 | Simon et al. | |
| 3,777,632 A | 12/1973 | Pepmeier | |
| 3,814,099 A | 6/1974 | Kobler | |
| 3,856,143 A | 12/1974 | Simon et al. | |
| 4,053,046 A | 10/1977 | Roark | |
| 4,170,305 A | 10/1979 | Hull, Jr. et al. | |
| 4,557,385 A | 12/1985 | Robinson | |

(Continued)

FOREIGN PATENT DOCUMENTS

| | | |
|---|---|---|
| EP | 213241 A | 3/1987 |
| EP | 226834 A | 7/1987 |

(Continued)

OTHER PUBLICATIONS

In the U.S. Appl. No. 12/621,764, the Restriction Requirement dated Aug. 10, 2012.

(Continued)

*Primary Examiner* — Lynne Anderson
*Assistant Examiner* — Kathryn E Ditmer

(57) ABSTRACT

A packaged elongate intravaginal device has an overwrap substantially enclosing the device. The overwrap has a longitudinal overlap seam disposed generally parallel to the longitudinal axis. The seam includes one ply of overwrap material disposed at a first margin of a overwrap blank superposed on a second ply of overwrap material disposed at a second margin of the overwrap blank, opposite the first. The overwrap has a substantially continuous line of weakness that intersects a plane including the longitudinal axis of the packaged device at at least three unique locations. The line of weakness extends across the longitudinal overlap seam and includes weakness components superposed in each ply of the overlap seam, and the line of weakness is arranged and configured in a manner to permit the overwrap to remain as a unitary structure upon destruction of the line of weakness.

5 Claims, 10 Drawing Sheets

U.S. PATENT DOCUMENTS

| | | |
|---|---|---|
| 4,610,659 A | 9/1986 | Friese |
| 4,617,781 A | 10/1986 | Ingersoll et al. |
| 4,648,513 A | 3/1987 | Newman |
| 4,765,477 A | 8/1988 | Froidh et al. |
| 4,816,100 A | 3/1989 | Friese |
| 4,881,644 A | 11/1989 | Norquest et al. |
| 5,054,264 A | 10/1991 | Miller |
| 5,133,457 A | 7/1992 | Kadel |
| 5,180,059 A | 1/1993 | Shimatani et al. |
| 5,365,719 A | 11/1994 | Council |
| 5,409,115 A | 4/1995 | Barkhorn |
| 5,462,166 A | 10/1995 | Minton et al. |
| 5,478,336 A | 12/1995 | Pigneul |
| 5,792,131 A | 8/1998 | Mizutani |
| 5,911,712 A | 6/1999 | Leutwyler et al. |
| 6,036,679 A | 3/2000 | Balzar et al. |
| 6,041,928 A | 3/2000 | Jousinen et al. |
| 6,053,318 A | 4/2000 | Petterson |
| 6,063,065 A | 5/2000 | Costa |
| 6,115,997 A | 9/2000 | Burrow |
| 6,183,457 B1 | 2/2001 | Kuhn |
| 6,250,468 B1 | 6/2001 | Huchel |
| 6,299,607 B1 | 10/2001 | Osborn, III et al. |
| 6,310,296 B1 | 10/2001 | Nishi et al. |
| 6,352,364 B1 | 3/2002 | Möbs |
| 6,446,795 B1 | 9/2002 | Allen et al. |
| 6,478,763 B1 | 11/2002 | Simonsen et al. |
| 6,955,665 B2 | 10/2005 | Domeier et al. |
| 6,994,696 B2 | 2/2006 | Suga |
| 7,065,939 B2 | 6/2006 | Wasson et al. |
| 7,073,666 B2 | 7/2006 | Arndt |
| 7,101,358 B2 | 9/2006 | Domeier et al. |
| 7,413,079 B2 | 8/2008 | Hermansson et al. |
| 7,422,105 B2 | 9/2008 | Loyd et al. |
| 2003/0065300 A1 | 4/2003 | Suga |
| 2003/0220624 A1 | 11/2003 | Domeier et al. |
| 2003/0220625 A1 | 11/2003 | Domeier et al. |
| 2003/0233813 A1 | 12/2003 | Leslie et al. |
| 2004/0133142 A1 | 7/2004 | Lochte et al. |
| 2007/0156109 A1 | 7/2007 | Loyd et al. |
| 2008/0058749 A1 | 3/2008 | Tackett et al. |
| 2008/0064581 A1 | 3/2008 | Lochte et al. |
| 2008/0105579 A1 | 5/2008 | Arndt |
| 2008/0118679 A1 | 5/2008 | McConnell et al. |
| 2009/0069769 A1 | 3/2009 | Minoguchi et al. |
| 2009/0188825 A1 | 7/2009 | McConnell |

FOREIGN PATENT DOCUMENTS

| | | |
|---|---|---|
| EP | 226834 B | 3/1992 |
| EP | 0 597 446 A | 5/1994 |
| EP | 807075 B | 11/1997 |
| EP | 1618860 A | 1/2006 |
| WO | WO 02/067837 A | 9/2002 |
| WO | WO 03/082174 A | 10/2003 |
| WO | WO 2004/080362 A | 9/2004 |
| WO | WO 2008/046036 A | 4/2008 |

OTHER PUBLICATIONS

In the U.S. Appl. No. 12/621,764, the Notice of Allowance dated Oct. 29, 2012.

TAMPON OVERWRAP

This application claims the benefit of U.S. provisional application 61/118,046 filed on Nov. 26, 2008, the complete disclosure of which is hereby incorporated herein by reference for all purposes.

FIELD OF THE INVENTION

The present invention relates to a wrapper for an individual absorbent article such as a tampon. In particular, the invention relates to a tampon wrapper provided with opening means that allows for removal of the tampon from the wrapper while keeping the wrapper as a unitary piece of material. The invention also includes a method of sealing the dome end of the tampon compatible with the opening means.

BACKGROUND OF THE INVENTION

Individual absorbent articles for personal hygiene articles are protected from the environment by sheets of material commonly referred to as wrappers or overwrap. Tampons, in particular, have employed wrappers in which each tampon is encased in a separate primary package, which may be then be sold in quantity in secondary packaging often a box.

Tampons are generally categorized in two classes: applicator tampons and digital tampons. The wrapper for an applicator tampon is typically elongated, loose, and flange or fin sealed at the ends with a small cut or notch at one end which the user uses to tear open the wrapper in a longitudinal fashion. The wrapper for a digital tampon is typically tight fitting, often contacting the outer surface of the tampon completely about the perimeter and sealed against the tampon at both the insertion and withdrawal end. This tight wrapping may help maintain the shape of the tampon and prevent deformation.

Over the years there have developed many issues with the wrappers for digital tampons. Sometimes the tampon has "relaxed" after compression and is difficult to remove from a wrapper due to the snugness of the fit. Some wrapper materials may actually stick to the outer surface of the tampon and be difficult to remove due to material interaction, causing the user to pry off the overwrap from the tampon. See, for example, WO 2004/080362. Other times, depending on the choice of material for the wrapper, there may be a static charge to the wrapper which causes the pieces of the wrapper to cling to the user's fingers after the wrapper seal has been broken and the tampon removed. Additionally, when a wrapper is separated into multiple pieces, it is annoying to have to keep those pieces together in one hand while trying to insert the tampon with the other hand.

Therefore, what is needed is a wrapper that can be removed from the enclosed tampon without difficulty and without the wrapper separating into multiple pieces of material.

SUMMARY OF THE INVENTION

We have found a packaged elongate intravaginal device that allows for removal of the device from the wrapper while keeping the wrapper as a unitary piece of material.

In one embodiment of the invention, a packaged elongate intravaginal device has an overwrap substantially enclosing the device. The overwrap has a longitudinal overlap seam disposed generally parallel to the longitudinal axis. The seam includes one ply of overwrap material disposed at a first margin of a overwrap blank superposed on a second ply of overwrap material disposed at a second margin of the overwrap blank, opposite the first. The overwrap has a substantially continuous line of weakness that intersects a plane including the longitudinal axis of the packaged device at at least three unique locations. The line of weakness extends across the longitudinal overlap seam and includes weakness components superposed in each ply of the overlap seam, and the line of weakness is arranged and configured in a manner to permit the overwrap to remain as a unitary structure upon destruction of the line of weakness. Preferably, at least a section of the line of weakness extends substantially continuously from the first margin of the overwrap blank to the second margin of the overwrap blank. In addition, the line of weakness may originate proximate a first end of the packaged device and extend toward a second end, opposite the first, of the packaged device. In another preferred embodiment, the line of weakness is inclined about 15° to about 45°.

In another embodiment, a packaged elongate intravaginal device has an overwrap substantially enclosing the device, and the overwrap has a substantially continuous line of weakness disposed about the device having an angle to a plane perpendicular to the longitudinal axis of the packaged device of about 20° to about 35°. The line of weakness originates proximate a withdrawal end of the packaged elongate intravaginal device with a ratio of open length to land length along the line of weakness of about 1:1 and a ratio of open length to land length along the line of weakness distal the withdrawal end of less than about 2:1.

In another embodiment of the invention, a method of opening a packaged elongate intravaginal device including the steps of: grasping an insertion end and a withdrawal end of the packaged elongate intravaginal device; twisting the ends in opposite directions about the longitudinal axis to fracture or otherwise rupture the line of weakness while maintaining the unitary structure of the overwrap; removing the withdrawal end of the overwrap from the elongate intravaginal device; grasping the withdrawal end of the elongate intravaginal device; removing the overwrap from the insertion end of the elongate intravaginal device; and inserting the elongate intravaginal device into a vagina. The overwrap preferably substantially encloses the device.

DETAILED DESCRIPTION OF THE PREFERRED EMBODIMENTS

Absorbent tampons usually incorporate elongate compressed absorbent structures, such as substantially cylindrical masses of compressed absorbent material having a central longitudinal axis and a radius that defines the outer circumferential surface of the tampon. Tampons are often formed by first obtaining a shaped mass of absorbent material called a tampon blank. This blank can be in the form of a roll of sheet-like material, a segment of a continuous absorbent material, a mass of randomly or substantially uniformly oriented absorbent material, an individually prepared or cast mass of absorbent material, and the like.

The tampon blank is relatively uncompressed and has a relatively low density. It is then compressed to form a product having overall dimensions less than those of the blank prior to use. The compressed tampons may have a generally uniform density throughout the tampon or they may have regions of differing density as described in Friese et al., U.S. Pat. No. 6,310,296, and Leutwyler et al., U.S. Pat. No. 5,911,712, the disclosures of which are herein incorporated by reference. Tampons also usually include a cover or some other surface treatment and a withdrawal string or other removal mechanism.

By 'outer surface' of the tampon it is meant herein the visible surface of the compressed tampon prior to use or expansion.

By 'length' of a tampon it is meant herein the linear extension of a tampon along its largest dimension.

By 'perimeter' of a tampon it is meant herein the distance measured along the outer surface of the tampon in a portion of said outer surface extending in a plane being substantially perpendicular to the dimension of the length of said tampon. In other words, the length of the tampon extends along the x-axis of an orthogonal Cartesian coordinate system and the perimeter typically lies in the y,z-plane of said coordinate system. While the exact measurements are not critical, examples of nominal diameters for tampons suitable in this invention range from 9 to 20 mm. Additionally, nominal lengths may be 40 to 60 mm.

The term "overwrap" as used herein refers to a structure, which is formed of a sheet of material and which substantially encloses an individual intravaginal device.

The term "intravaginal device" may mean those devices designed to be placed within the vaginal canal such a tampon, or incontinent/pessary device.

As used herein, the terms "weakness component" and "line of weakness" shall mean a series of weakness elements arranged in a row. These weakness elements may be perforations, areas of reduced thickness, slits, score lines, areas of reduced density, etc. The line of weakness may be perforated mechanically or scraped ultrasonically or with a laser.

Figure 1:
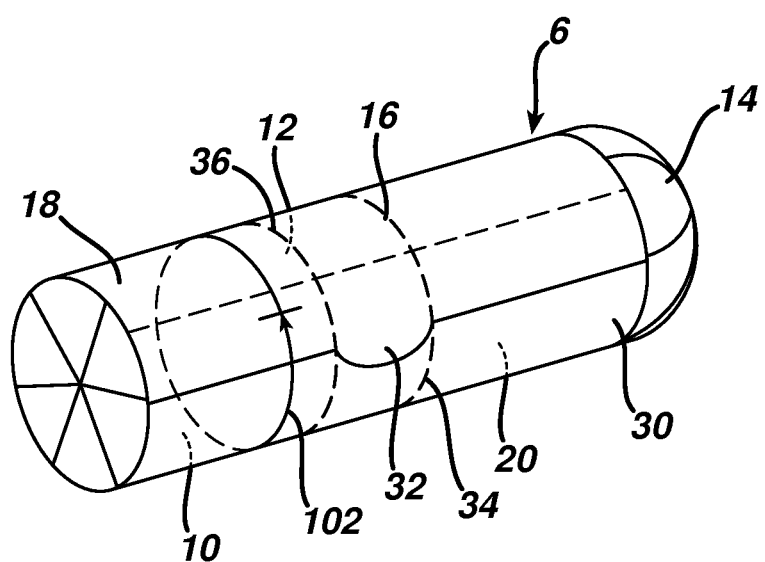
FIG. 1 is a perspective view of a tampon of the prior art.

An example of a packaged tampon 6 known in the prior art is illustrated in FIG. 1. The packaged tampon 6 contains tampon 10 within an overwrap 30. Tampon 10 has a compressed, elongate absorbent structure 12 having an insertion end 14, a withdrawal end 18 and a central portion 16 located between the insertion end and withdrawal end. Tampon 10 has an outer surface 20 and perimeter 102, which extends 360° around the tampon.

In the example shown in FIG. 1, the overwrap 30 has an opening mechanism. In this example of prior art, the overwrap has a finger lift tab 32, which allows the user to tear open the overwrap along perforated lines 34 and 36 that extend around the overwrap. Typically, this type of opening mechanism results in the overwrap being torn into multiple portions—a central portion having a width which corresponds to the finger lift dimension, a portion covering the insertion end and a portion covering the withdrawal end. Once the user has opened the overwrap by lifting and separating the finger lift tab, the user may additionally have to peel off the remaining portions. This remains an inconvenience for the user as she now has to use both hands to unwrap the tampons while dealing with the multiple pieces, which may have static charges causing the pieces to cling to her hands, her fingers, and/or the tampon. This can increase the risk of the overwrap remaining on the tampon when it is inserted into the user's body. This remaining piece of overwrap may disengage from the tampon as the tampon absorbs fluid, thereby remaining in the body until removed by the user.

This uncontrolled opening of the wrapper may also occur in thinner packaging materials in which the tear may not follow a predetermined path along a line of weakness and may also result in multiple pieces of the destroyed wrapper.

The wrappers can generally be formed of a sheet or one connected piece of overwrap material, though an overwrap can be made from multiple pieces of material sufficiently joined together such that they substantially act as a single sheet or one connected piece of overwrap material. In the prior art example of FIG. 1, the material is joined together by any means known in the art. Where the material is joined is commonly referred to as a seam. The overwrap may be clear, colored, or have printed graphics which may include directions for opening (arrows, dotted lines, etc.). Typically, suitable wrapper materials for use herein are flexible polymeric films and may have any thickness. Additionally, the surface of the overwrap including the seam may have printing. When printing on the overwrap, including the seam, the perforations may become more distinct to the user.

Figure 2:
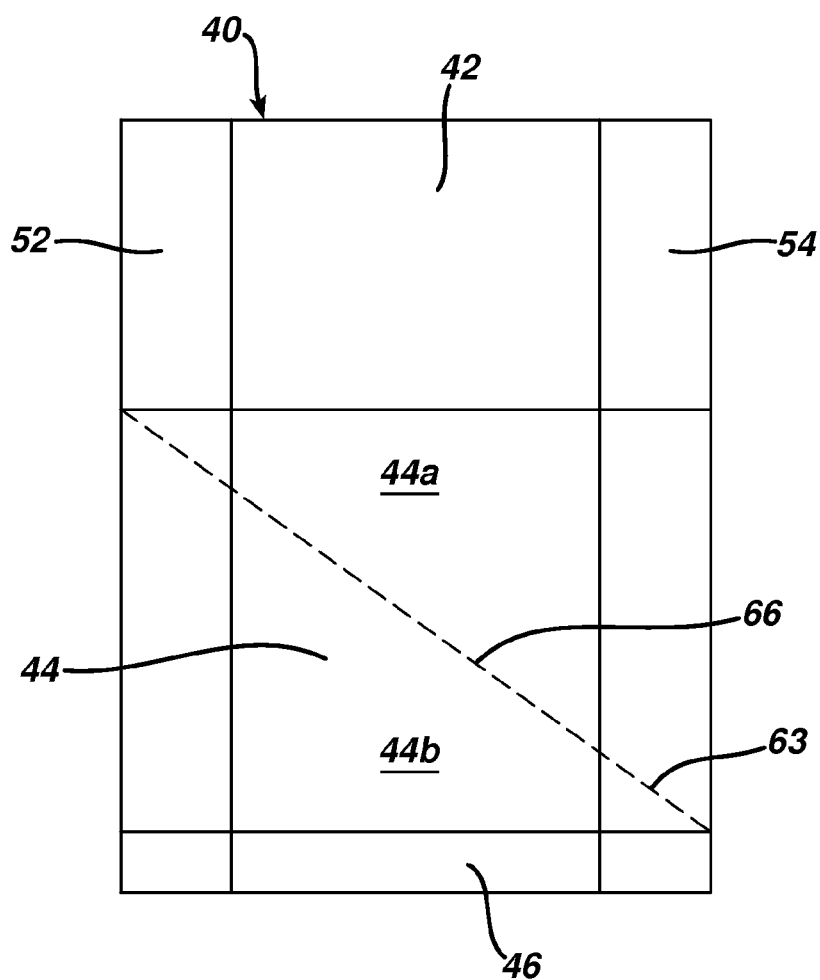
FIG. 2 is a plan view of one embodiment of the present invention showing a sheet of overwrap material including weakness components.

Turning to FIG. 2, there is shown a sheet of overwrap, which is used to form one embodiment of the present invention.

As shown in this figure, the wrapper may be formed from a rectangular sheet of material 40 having an insertion end 42, a withdrawal end 46, a central portion 44, a first margin 52 and a second margin 54. The central portion 44 further has upper central area 44a, which is toward the insertion end and lower central area 44b, which is toward the withdrawal end. When sheet 40 is formed into a tube, margins 52 and 54 overlap. These margins may be joined together longitudinally (resulting in a seam down the side of the tampon). The sealing of the margins form a two layer seam.

Figure 3:
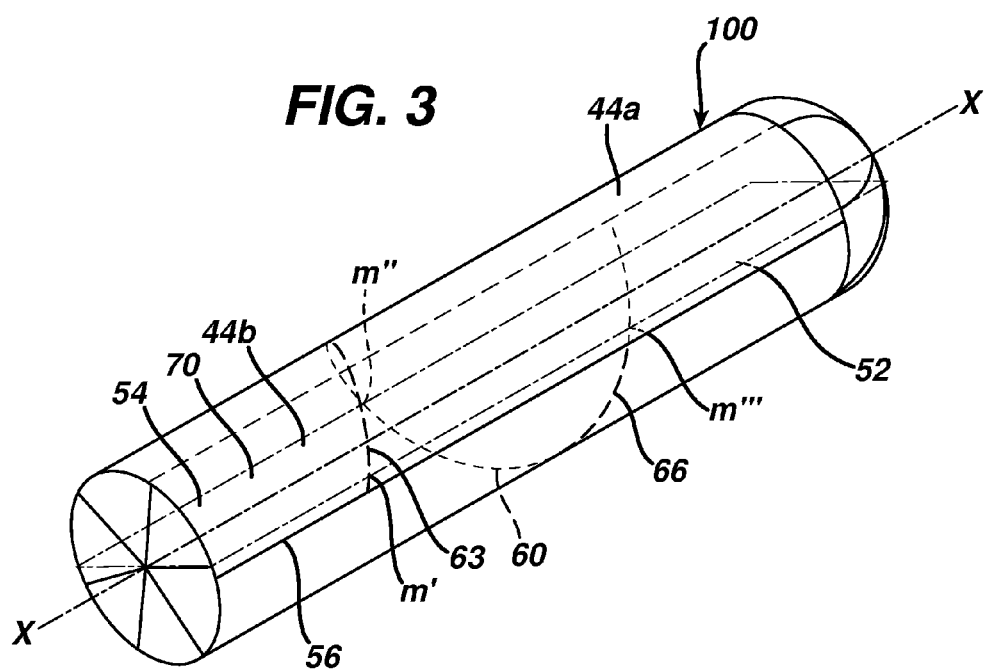
FIG. 3 is a perspective view of a wrapped tampon made from the sheet of material of FIG. 2 according to the present invention.

In this embodiment, there is a single line of weakness made of weakness components 66 and 63. In the embodiment shown in FIG. 2, weakness component 66 is shown as inclining or at a diagonal direction. A tampon contained with the resultant overwrap is shown in FIG. 3.

Additionally by using a specific ratio of weakness:land lengths in specific areas of the overwrap, it is possible to provide an overwrap that opens completely around the tampon, remains in a single unitary piece but provides for hygienic removal of the tampon from the overwrap. For example, using a slit or perforation having an open length as the weakness element, it has been found that a ratio in the range, for example, of approximately 1:1, e.g, about 2:3 to about 3:2, preferably about 4:5 to about 5:4 open length:land length in lower central area 44b (including weakness component 63) and a ratio, for example, of open length to land length in upper central area 44a of at least about 2:1 allows for the user to grasp the insertion end and the withdrawal end with fingers from both hands, twist, pull, and/or bend on the overwrap and open the upper central area 44a with a small amount of force. The user would then continue to slightly twist the overwrap to further split the line of weakness into the lower central area 44b. The user can then pull to remove the overwrap from the base with one hand while holding the insertion end. The overwrap on the insertion end remains intact without the user's fingers contacting the tampon. The overwrap remains as a single piece of material. Since the perforations in the upper central area 44a have a greater open length as compared to the open length of the lower central area 44b, the line of weakness will generally open first in the upper central area 44a (corresponding to a central portion of the packaged tampon) before opening in the lower central area 44b (corresponding to the lower end of the packaged tampon). The insertion end of the tampon would remain in the overwrap until the user completely removed the overwrap (just prior to insertion into the body). Of course, the steps of twisting open and pulling off the overwrap can be accomplished in one step. While the above details an example of a ratio for one type of material, the choice of material and basis weight can alter the ratio of open area to land region. The above provides examples of open lengths, land lengths and the ratios between them. In one embodiment, the open length:land length ratio is balanced so the formed line of weakness is stronger at withdrawal end and weaker in center portion of the packaged tampon. In another embodiment, the open length;land length is consistent throughout the perforation line. Any ratio that obtains this is for a particular material and a particular sized tampon is acceptable, however, the line of weakness should be optimized to permit the overwrap to withstand 1) internal expansion forces from the tampon as the compressed fibers tend to relax over time and 2) external forces from the environment (such as those exerted on the overwrap when a consumer stores the tampon in a purse or pants pocket) without rupturing the line of weakness and 3) processes in manufacturing. In one preferred embodiment, the twisting force needed to rupture the line of weakness is less than about 25 Newtons ("N").

Weakness components 66 have an open length to land length ratio of approximately 2:1 and are located primarily in the upper central area 44a. In one embodiment, the open length to land length in the upper central area 44a is 900:400 (μm) and the open length to land length in the lower central area 44b is 450:550 to 500:500 (μm).

Additionally, weakness components 66 may incorporate multiple sets of open length to land length to form perforation patterns. For example, in one embodiment starting from lower central area 44, the open length:land length ratio may be 450:500. As the perforation line enters area 44a, the open length:land length ratio may become 800:500, then 900:400, and finally back to 800:500.

The line of weakness does not necessarily have to be straight. As formed in the overwrap, the weakness components and resultant line of weakness may be a diagonal line, a curved line or a line that changes direction by e.g. having angles, curves, and/or inflections such as inflection points. In order to obtain the line of weakness in this type of embodiment, the sheet of material will need to have the weakness components in the appropriate pattern. In one embodiment, the line of weakness originates in the withdrawal portion of the tampon and inclines such that it terminates in the central portion. In particular, the line of weakness can be inclined at an angle from the plane perpendicular to the longitudinal axis.

Figure 4:
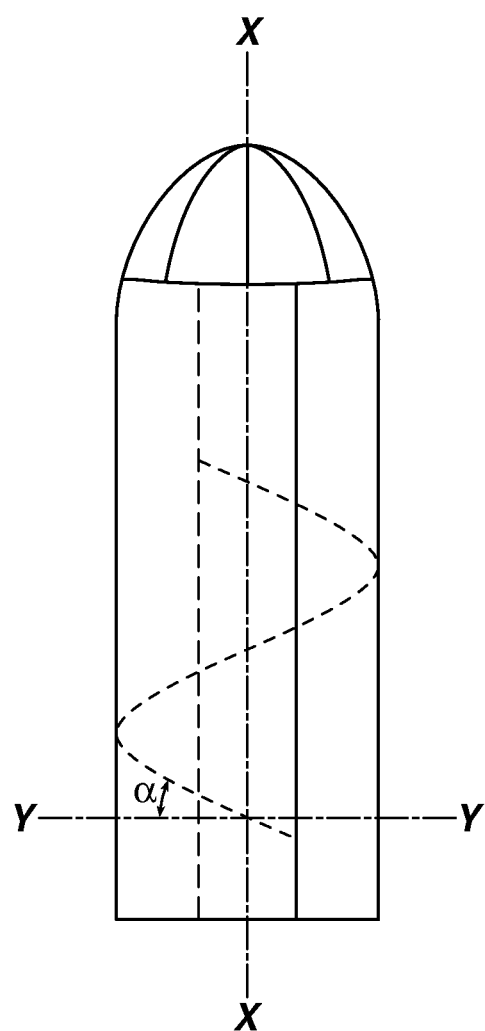
FIG. 4 is a plan view of an embodiment showing the longitudinal axis and a plane, which is perpendicular to the longitudinal axis.

This is shown in FIG. 4 with angle α formed by the line of weakness to a plane Y-Y extending perpendicular to longitudinal axis X-X. In another embodiment, the line of weakness originates in the lower 5-25% (lower central area 44b) of the sheet and terminates in the upper central area 44a (shown FIG. 2). The angle of inclination is balanced against the desire to maintain the wrapper in a single piece. The smaller the angle, the greater the component of force applied to the package is translated into shear force that is able to rupture the line of weakness. However, a small angle of inclination provides greater opportunity for the wrapper material to tear between the ends of the line of weakness to result in two separated package remnants. The larger the angle, the lesser opportunity for the wrapper material to tear between the ends of the line of weakness to result in two separated package remnants. However, more twisting circumferential force may be required to rupture the line of weakness. We have found that an angle of about 5° to about 45° is useful and that an angle of about 20° to about 35° is preferred to balance the properties discussed above. As tampons come in varying sizes in order to provide various absorbencies, the sheet used to wrap the tampon may have different dimensions. Often the larger absorbencies will require larger tampons therefore requiring a larger sheet of overwrap. The zone that is actually perforated will also increase as the size of the overwrap sheet does, thereby allowing the line of weakness to traverse a greater area. The perforation zone is that central area 44 shown in FIG. 2. For example, with a o.b.® light absorbency tampon (Germany) perforation angle may be 29° which results in a perforation zone that extends for 23.5 mm. Using the same angle)(29° for a o.b.® super plus absorbency tampon (Germany) results in a perforation zone of 34 mm. Other examples are shown in the table below.

TABLE 1

| Tampon | Angle | Perforation Zone (mm) |
|---|---|---|
| o.b. ® light absorbency tampon (Germany) | 32.5 | 27 |
| o.b. ® mini tampon (Germany) | 32.5 | 27 |
| o.b. ® normal absorbency tampon (Germany) | 29 | 27 |
| o.b. ® super absorbency tampon (Germany) | 26 | 27 |
| o.b. ® super plus absorbency tampon (Germany) | 23.7 | 27 |
| o.b. ® light absorbency tampon (Germany) | 29 | 23.5 |
| o.b. ® mini tampon (Germany) | 29 | 23.5 |
| o.b. ® normal absorbency tampon (Germany) | 29 | 27 |
| o.b. ® super absorbency tampon (Germany) | 29 | 30.5 |
| o.b. ® super plus absorbency tampon (Germany) | 29 | 34 |

In still another embodiment, the line of weakness is not a straight line but a curved line that originates in the lower central area 44b, extends into the upper central area and terminates in the lower central area (not shown). In these embodiments, the withdrawal end portion of the overwrap is easily removed after the line of weakness has been ruptured, which leaves the insertion portion of the overwrap somewhat intact. This allows the user to further handle the tampon without actually contacting or contaminating the insertion end of the tampon.

In a preferred embodiment, the line of weakness according to the present invention extends completely around the perimeter of the tampon. As used herein, the term "extends completely around the perimeter" shall mean that the line of weakness is continuous 360° about the circumference of the outer surface 20 of the intravaginal device.

When placed on a tampon, the overwrap has a continuous line of weakness which includes the two layer seam. The line of weakness therefore extends completely around the perimeter of the encased tampon. When used to wrap the tampon, the overwrap has a line of weakness that may have one end near the withdrawal end 18 of the tampon and another end disposed toward the insertion end 14. In one embodiment, the line of weakness is arranged and configured such that when the resulting overwrap is opened, the portion holding the insertion end of the tampon remains on the tampon and the portion holding the withdrawal end of the tampon also remains on the tampon but can be easily pulled off.

The overlapping of the margins and sealing does not compromise the line of weakness such that when the user opens the overwrap, the line of weakness tears completely around and through the sealed overwrap. The seal does not prevent the line of weakness from extending and performing through overlap region. If the line of weakness is formed from a series of slits, the forming of the seam in the margins will not close up the slits; rather the slits are sufficiently open to be easily ruptured.

Upon the rupturing of the line of weakness, the resultant open overwrap can be removed as a unitary piece of material. As the line of weakness originates and end at different parts of the seam, the line of weakness will not cause division of the wrapper into separate pieces upon opening. The end and origin of the line of weakness are sufficiently separated so as to not overlap.

FIG. 3 shows material sheet 40 wrapped around tampon 10 to form overwrap 100. Margins 52 and 54 overlap and are joined to form a two layer seam 70. There is one continuous line of weakness 60. The joining of margins 52 and 54 to form the two layer seam 70 does not eliminate or close the weakened areas, especially the weakened components.

The seam not only connects the layers of material together but provides a barrier which prevents contaminants from penetrating into the packaged article. The seam may be any thickness depending on the materials being joined together and the outer conditions. For example, a seal that is expected to provide water protection may be thicker than a seal used to prevent air penetration (for example, the seal used to wrap dry foodstuffs). In this invention, the thickness of the seal or seam is not critical.

Seam 70 may have any dimension that securely holds the overlaid margins together. While it is preferred that the edge of the margin forming the outer surface is securely sealed against the lower material, it is not necessary for the seam to extend to the edge.

In the embodiment shown in FIG. 3, the second margin overlays the first margin and partially forms the outer surface of overwrap 100. The overwrap is substantially a tube-like cylinder. Both ends are closed such that the tampon within the overwrap is completely contained within the overwrap and separated from the environment. Seam 70 extends to edge 56 of margin 54 and forms a relatively smooth surface. The intravaginal device in this figure has longitudinal axis XX, which extends through insertion end 42 to withdrawal end 46.

Shown in FIG. 3 is a plane extending outward from and including longitudinal axis XX. The line of weakness intersects this plane at at least three unique locations, as the line of weakness extends at least 360° around the perimeter of the tampon. In the embodiment of FIG. 3, the unique locations include where the plane intersects the two weakness components in the wrapper margins and the weakness component located between the margins. Thus, the plane intersects the line of weakness at at least three unique locations—m', m", m'".

The longitudinal seam is a longitudinal attachment zone, which connects the overlapping margins (52 and 54) together. In this invention, the longitudinal attachment zone need not be a single, continuous seal line but rather may be multiple seals lines which are discontinuous and off-set to each other. This will be further explained below.

In this embodiment, there are two weakness components identified in FIG. 2 as elements 63 and 66. Weakness component 63 is mainly in the lower central area 44b of margins 54. In one embodiment, at least one of the weakness component 63 becomes weakness component 66 and extends beyond the respective margin into the central portion 44. Weakness component 66 extends from margin 54 and into margin 52. In the embodiment shown in FIG. 2, weakness component 66 is shown as inclining or at a diagonal direction. The weakness component may have different characteristics in margin and central area. In particular, the weakness component in the central portion 44 may be weaker than the weakness component in the withdrawal end 46 of the tampon.

In one embodiment, the ends of the overwrap have a surface textured or embossment. For example, the insertion and withdrawal end may be printed with a pattern made from an anti-slippery lacquer or may be mechanically or ultrasonically embossed such that the ends have a pattern. The pattern may improve the grip or handling of the packaged tampon.

The seam may be formed by any means known in the art; however, it is important as previously stated that the open areas of the line of weakness not be compromised significantly.

Figure 5:
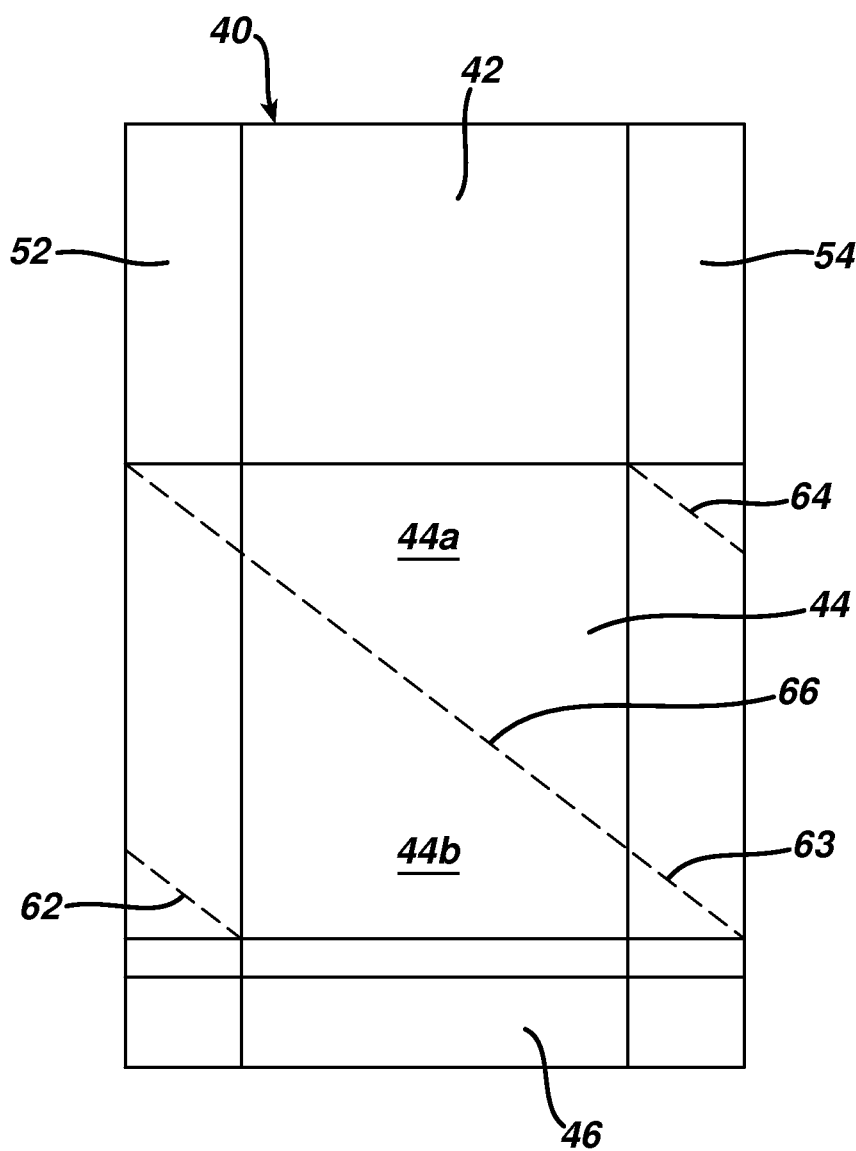
FIG. 5 is a plan view of another embodiment of the present invention showing a sheet of overwrap material including weakness components.
Figure 6:
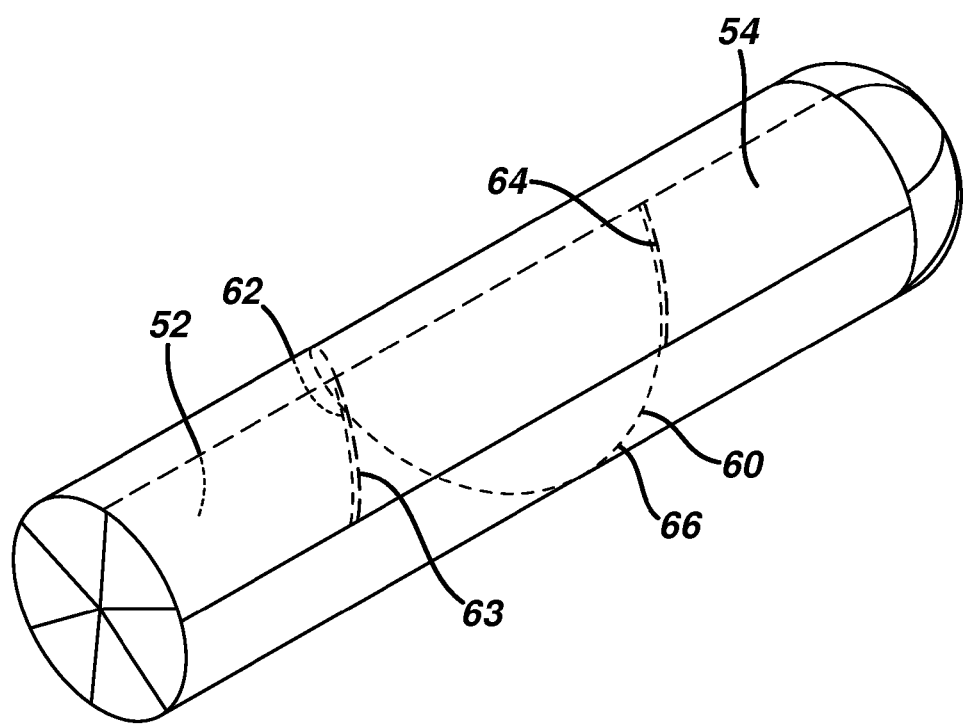
FIG. 6 is a perspective view of a wrapped tampon made from the sheet of material of FIG. 5 according to the present invention.

Another example of a sheet of overwrap is shown in FIG. 5. In this embodiment, there are multiple weakness components, two of which need to be in the margins. As shown, there are multiple weakness components—62, 63, 64 and 66. Weakness component 62 is in margin 52, weakness components 63 and 64 are in margin 54. Weakness component 66 extends from margin 52 to the edge of margin 54. As in the previous FIG. 2, the weakness components form a single of weakness 60 (shown FIG. 6) when formed into a tube, which ultimately holds a tampon. The wrapping is done such that weakened components are registered to each other and overlap to form one continuous line of weakness 60.

As previously stated, when sheet 40 is formed into a tube for holding a tampon, margins 52 and 54 overlap and are joined to form a two layer seam 70. In one embodiment, sheet 40 is a single ply of material such that when margins 52 and 54 are overlapped, the two layer seam has two plies. The wrapping is done such that weakness components are registered to each other and overlap to form one continuous line of weakness (similar to the packaged tampon shown in FIGS. 3). The joining or sealing of margins 52 and 54 to form the two layer seam does not eliminate or close the weakened areas.

Figure 7:
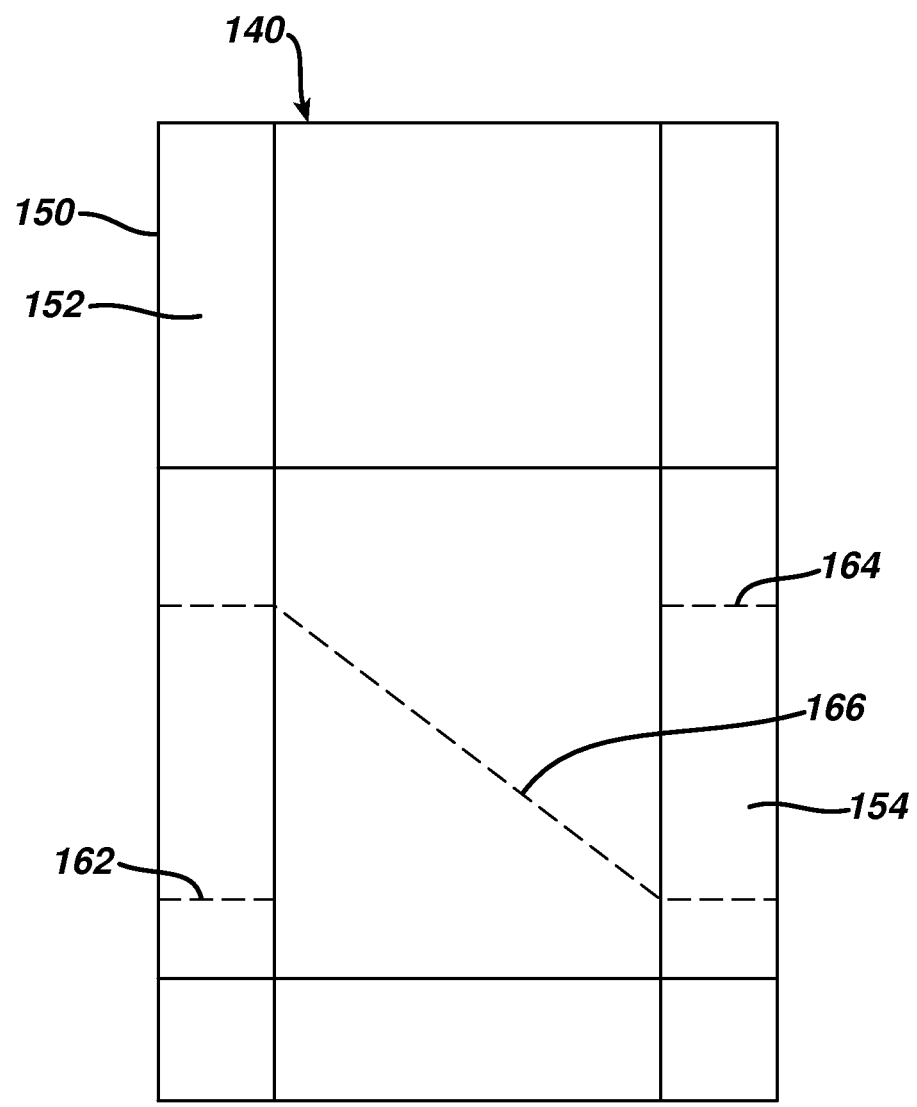
FIG. 7 is a plan view of still another embodiment of the present invention showing a sheet of overwrap material including weakness components.
Figure 8:
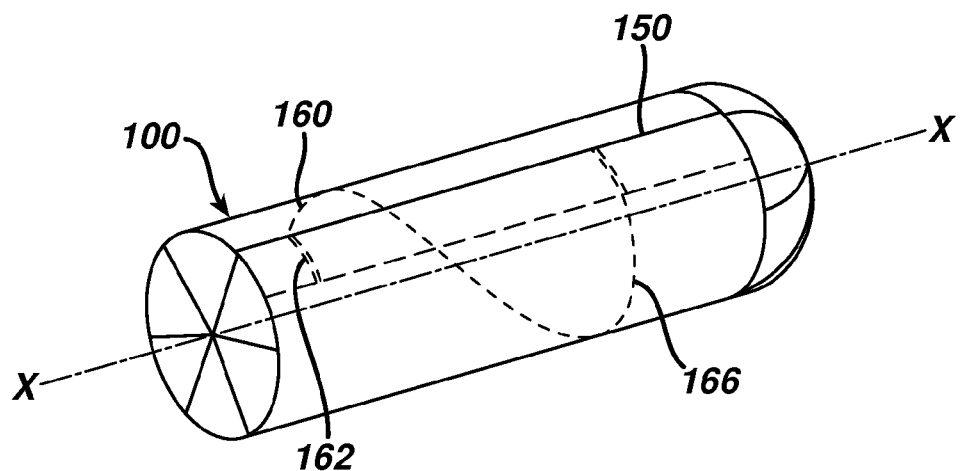
FIG. 8 is a perspective view of a wrapped tampon made from the sheet of material of FIG. 7 according to the present invention.

In FIG. 7, another embodiment is shown with the first margin overlaying the second margin to partially form the outer surface of overwrap 100. In this embodiment, the weakness component begins in margin 154 as a horizontal line which then inclines diagonally toward margin 152. In margin 154, weakness component 164 and in margin 152, weakness component 162, each are horizontal and aligned such that when the sheet 140 is wrapped about a cylindrical intravaginal device, they overlay weakness component 166 to form a continuous line of weakness 160 (shown FIG. 8). Edge 150 of margin 152 partially forms the outer surface of the overwrap 100.

While the above details a single line of weakness, it is possible to have multiple lines of weakness such that the overwrap initially opens in numerous spots in the central portion.

Opening of the wrapper for releasing the tampon 10 along the line of weakness 160 results in an initial tearing step, during which the overwrap 100 mainly tears diagonally or at an incline around the perimeter of the tampon 10 and a subsequent step, during which the tampon is removed from the opened overwrap 100. The diagonal opening of the overwrap results in a large open area, which allows for the tampon to be easily removed with little manipulation. The opened overwrap remains in a unitary piece, which provides for easy removal and disposal with one hand. The problem of having multiple small pieces of wrapper clinging to the user's fingers or falling into a toilet is thereby eliminated.

It is generally preferred according to the present invention that the distance between adjacent weakness elements is substantially equal throughout the line of weakness. However, if desired, varied spacing can be employed to affect the tearing force profile (increase/decrease of tearing force upon tear propagation) experienced by the user as she opens the wrapper along the line of weakness. A particularly preferred embodiment of the line of weakness of the present invention is a line of weakness extending completely around a part of the perimeter of the wrapped tampon, and in some embodiments, the line of weakness extends more around more than the perimeter of the wrapped tampon.

The absorbent materials useful in the formation of the absorbent body include fiber, foam, superabsorbent, hydrogels, and the like. Preferred absorbent material for the present invention includes foam and fiber. Absorbent foams may include hydrophilic foams, foams which are readily wetted by aqueous fluids as well as foams in which the cell walls that form the foam themselves absorb fluid.

The tampon blank may be substantially surrounded or enclosed by a fluid-permeable cover. Thus, the cover encloses a majority of the outer surface of the tampon. This may be achieved as disclosed in Friese, U.S. Pat. No. 4,816,100, or Lochte; et al., US Publ. App. No. US 2008-0064581 A1, entitled "Tampon Having Apertured Film Cover Thermobonded to Fibrous Absorbent Structure", the disclosures of which are herein incorporated by reference. In addition, the insertion end 14 of the tampon, the opposite withdrawal end 18, or both may be enclosed by the cover. Of course, for processing or other reasons, some portions of the surface of the tampon 10 may be free of the cover. For example, the insertion end 14 of the tampon 10 and a portion of the cylindrical surface adjacent this end may be exposed, without the cover to allow the tampon 10 to more readily accept fluids.

The cover may be a nonwoven or apertured polymeric film. The cover can ease the insertion of the tampon 10 into the body cavity and can reduce the possibility of fibers being separated from the tampon 10.

Examples for wrapper materials suitable for use with the present invention are polymeric films made of polyethylene, polypropylene, polyester, cellophane, polyamide, poly(vinyl chloride), ethylene-vinyl acetate copolymer and the like. Alternatively, heat-shrinkable films, stretch films or prestretched elastic material can be used to form the wrapper of the present invention. While not limited to a given composition, preferred compositions of heat-shrinkable and stretch films comprise primarily polyolefins such as polyethylene and polypropylene, or poly(vinyl chloride). Polystyrene and polyethylene-terephtalate (PET), although being not heat sealable, are also suitable for use with the present invention. In one embodiment of the present invention, the wrapper material is formed from a coextruded polypropylene film. Wrappers consisting of those materials can also be closed by gluing with an adhesive. Other generally occlusive materials include metallic foils, such as aluminum foil. While occlusive wrapper materials are often preferred, in other situations non-occlusive or porous materials can be used, such as nonwovens, wovens, scrims, meshes and papers. Such non-occlusive materials can be made occlusive by combinations such as by lamination with or by coating with occlusive material. In the case of cellulosic papers, examples include lamination with a polymeric film such as a polyolefinic composition or coating or impregnation of the paper with wax. The aforementioned materials can be coated with various chemical compounds to improve their barrier properties or the ability for sealing. Any suitable combination of the aforementioned materials is also within the scope of the present invention. In one embodiment, the over wrap material is a matt transparent, heat-sealable, one side treated OPP film available from Treofan (Treofan Germany GmbH & Co. KG. Am Prime Parc 17, 65479 Raunheim, Germany) named Treofan Crystal—GNR.

In some embodiments, the materials suitable for use as wrapper materials with the present invention are heat-sealable for forming the wrapper by closing the wrapper material via heat-sealing onto itself after having wrapped the tampon. Thereby a seam is generated in the regions of the wrapper, which were exposed to heat. Alternatives for closing the wrapper material are gluing, embossing, crimping, sewing, stitching, entangling, mechanical interlocking, cold pressure welding, or ultrasonic bonding. In some embodiments, the wrapper materials for use herein have a low flexural modulus for providing a low noise tampon wrapper during transport as well as during handling, i.e. opening of the wrapper.

Figure 9:
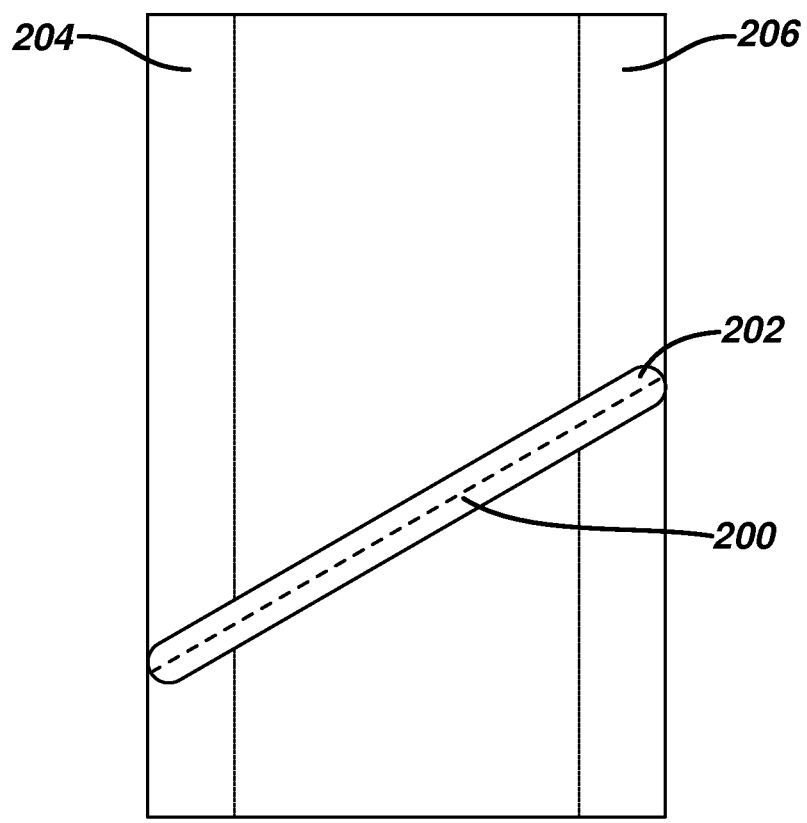
FIG. 9 is a plan view of still another embodiment of the present invention showing a sheet of overwrap material including weakness components and a coating.

The surface of the over wrap material may be coated to provide a sealing/protection to any printing contained on the surface of the sheet. The coating may also aid in providing a frictional grip (increasing the co-efficient of friction, as discussed above) and in processing (some inks or coating may result in a sticky surface). In one embodiment, the overwrap sheet is coated with a finish from Siegwerk Drckfarben AG (Alfred-Keller-Strasse 55, 53721 Siegburg, Germany) sold under the name of Mr Varnish Masterbatch-MB00. It is important that the coating does not significantly inhibit the sealing of the overlap seam, or the seam may not be secure enough for the intended use. However, in one embodiment shown in FIG. 9, the line of weakness 200 has a corresponding printed line 202 that overlays or runs adjacent the perforations, even in the margins 204, 206. As the printed line may extends into at least one margin, the coating also is present in the at least one margin to help maintain the weakness in the seam area for easy opening.

Figures 10, 11:
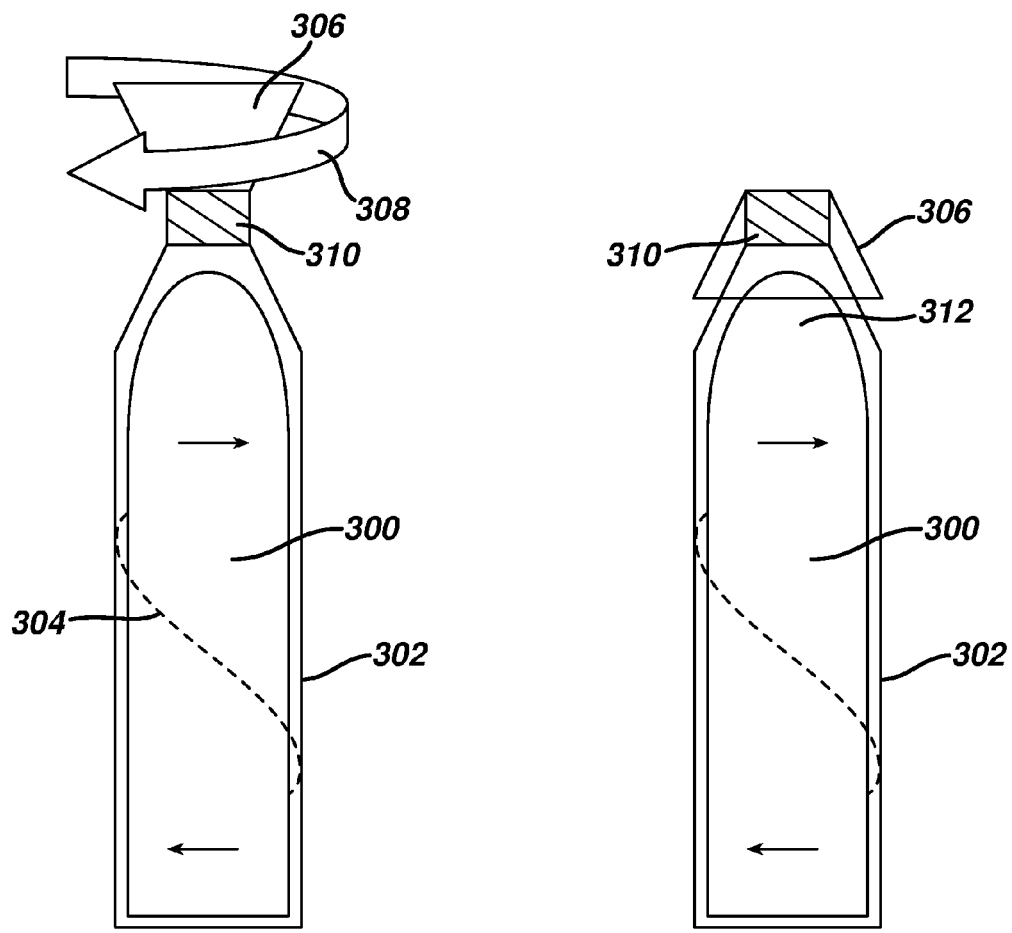
FIG. 10 is a side elevation of the machine twist direction of the rounded end of the over wrapped tampon.
FIG. 11 is a side elevation of the finished packaged tampon of FIG. 10.

In currently available tampons, the over wrap may be placed on the tampon as disclosed for example, U.S. Pat. No. 3,856,143 (Simon). Simon discloses a process and apparatus for twist closing one end of a tubular overwrap containing a tampon with a rounded head directed toward the end of the wrapper being closed and excess tubular wrapper material extending past the rounded head. It has been surprising found that the direction of the overwrap closure twist in relation to the direction of the incline of the line of weakness on the overwrap affects the integrity of the overwrap during further processing. If the twist occurs in the direction of a rising line of weakness (e.g. clockwise as shown in FIG. 10), the overwrap is less likely to be weakened than if the twist were to occur counter-clockwise, as this is the direction the consumer will twist the package to open it for use. Thus, a tampon 300 is enclosed in an overwrap 302 with a line of weakness 304 rising in a clockwise direction. The upper end 306 of the overwrap 302 is twisted in a clockwise direction shown by arrow 308 to form a twist closure 310. As shown in FIG. 11, the excess material of the upper end 306 of the overwrap 302 is folded over the domed end 312 of the tampon 300, generally as described in Simon U.S. Pat. No. 3,856,143.

Also included in this invention is a method of opening a tampon packaged within an overwrap made according to the description above. In this method, the tampon or intravaginal device has a longitudinal axis and is substantially enclosed by the overwrap, the overwrap has a longitudinal overlap seam disposed generally parallel to the longitudinal axis and the overwrap is one ply of material disposed at a first margin of a overwrap blank superposed on a second ply of overwrap material disposed at a second margin of the overwrap blank, opposite the first, where the overwrap has a substantially continuous line of weakness that intersects a plane including the longitudinal axis of the packaged device at at least three unique locations. The user would grasp the two ends of the intravaginal device and twist, pull and/or bend in opposite directions in order to rupture the continuous line of weakness. Slightly pulling on the withdrawal portion of the overwrap, the user removes the overwrap, exposing the central and withdrawal portions of the intravaginal device. The user can then further manipulate the intravaginal device—e.g., expand the withdrawal end (aids digital insertion). Once this is done, the user can grasp the withdrawal end, remove the overwrap from the insertion end and insert the tampon into the body cavity.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A packaged elongate intravaginal device having a longitudinal axis comprising:
    a. the elongate intravaginal device; and
    b. an overwrap substantially enclosing the elongate intravaginal device and having a longitudinal overlap seam disposed generally parallel to the longitudinal axis, wherein:
        i. the seam includes one ply of overwrap material disposed at a first margin of a overwrap blank, an inner surface of which is superposed on an outer surface of a second ply of overwrap material disposed at a second margin of the overwrap blank, opposite the first;
        ii. the overwrap has a substantially continuous line of weakness that extends from the first margin to the second margin and at least 360° around the circumference of the elongate intravaginal device;
        iii. the line of weakness extends across the longitudinal overlap seam and includes weakness elements superposed in each ply of the overlap seam; and
        iv. the line of weakness does not intersect itself, thereby remaining a unitary structure upon destruction of the line of weakness.

2. The packaged elongate intravaginal device of claim 1, wherein the line of weakness originates proximate a first end of the packaged device and extends toward a second end, opposite the first, of the packaged device.

3. The packaged elongate intravaginal device of claim 1, wherein the line of weakness is inclined about 15° to about 45° from a plane perpendicular to the longitudinal axis.

4. A packaged elongate intravaginal device having a longitudinal axis comprising:
    a. the elongate intravaginal device; and
    b. an overwrap substantially enclosing the elongate intravaginal device and having a longitudinal overlap seam including one ply of overwrap material disposed at a first margin of an overwrap blank, an inner surface of which is superposed on an outer surface of a second ply of overwrap material disposed at a second margin of the overwrap blank, opposite the first, the overlap seam disposed generally parallel to the longitudinal axis, wherein:
        i. the overwrap has a substantially continuous line of weakness comprising open and land portions, each having a length associated therewith, disposed about the device having an angle to a plane perpendicular to the longitudinal axis of the packaged device of about 20° to about 35° ;
        ii. the line of weakness originates proximate a withdrawal end of the packaged elongate intravaginal device with a ratio of open length to land length along the line of weakness of less than about 3:2 and a ratio of open length to land length along the line of weakness distal the withdrawal end of at least about 2:1.

5. The packaged elongate intravaginal device of claim 4, wherein the ratio of open length to land length along the line of weakness proximate the withdrawal end is less than about 5:4.

* * * * *